United States Patent [19]
Lee et al.

[11] Patent Number: 5,870,449
[45] Date of Patent: *Feb. 9, 1999

[54] OPERATOR CONSOLE FOR ARTICLE INSPECTION SYSTEMS

[75] Inventors: Bruce S. Lee, Waltham; Jason Anderson, Cambridge; Michael P. Ellenbogen, West Newton, all of Mass.

[73] Assignee: Vivid Technologies, Inc., Woburn, Mass.

[*] Notice: The term of this patent shall not extend beyond the expiration date of Pat. No. 5,699,400.

[21] Appl. No.: 880,575

[22] Filed: Jun. 23, 1997

Related U.S. Application Data

[63] Continuation of Ser. No. 647,043, May 8, 1996, Pat. No. 5,699,400.

[51] Int. Cl.⁶ ................................................. G01N 23/04
[52] U.S. Cl. ................................................................ 378/57
[58] Field of Search ........................................ 378/57–62

[56] References Cited

U.S. PATENT DOCUMENTS

| | | | |
|---|---|---|---|
| 3,848,130 | 11/1974 | Macovski | 250/336 |
| 3,884,816 | 5/1975 | Takahashi | 250/359 |
| 4,722,096 | 1/1988 | Dietrich et al. | 378/57 |
| 4,736,401 | 4/1988 | Donges et al. | 378/146 |
| 4,748,645 | 5/1988 | Dönges et al. | 378/19 |
| 4,756,015 | 7/1988 | Doenges et al. | 378/57 |
| 4,759,047 | 7/1988 | Donges et al. | 378/99 |
| 4,783,794 | 11/1988 | Dietrich | 378/57 |
| 4,788,704 | 11/1988 | Donges et al. | 378/99 |
| 4,841,554 | 6/1989 | Doenges et al. | 378/57 |
| 4,866,424 | 9/1989 | Parks | 340/551 |
| 4,870,670 | 9/1989 | Geus | 378/87 |
| 4,884,289 | 11/1989 | Glockmann et al. | 378/57 |
| 4,987,584 | 1/1991 | Doenges | 378/100 |
| 5,016,173 | 5/1991 | Kenet et al. | 364/413.13 |
| 5,018,178 | 5/1991 | Katsumata | 378/4 |
| 5,031,226 | 7/1991 | Delange | 382/22 |
| 5,044,002 | 8/1991 | Stein | 378/54 |
| 5,065,418 | 11/1991 | Bermbach et al. | 378/57 |
| 5,091,924 | 2/1992 | Bermbach et al. | 378/57 |
| 5,182,764 | 1/1993 | Peschmann et al. | 378/57 |
| 5,319,547 | 6/1994 | Krug et al. | 364/409 |
| 5,367,552 | 11/1994 | Peschmann | 378/4 |
| 5,379,334 | 1/1995 | Zimmer et al. | 378/98.2 |
| 5,490,218 | 2/1996 | Krug et al. | 382/100 |
| 5,699,400 | 12/1997 | Lee et al. | 378/57 |

OTHER PUBLICATIONS

"Recoginita Plus", SZKI Recoginita Corp., 1991.

*Primary Examiner*—David P. Porta
*Attorney, Agent, or Firm*—Cooper & Dunham LLP

[57] ABSTRACT

The present invention provides an inspection system having a scanner system coupled to an operator console. The scanner system is preferably an x-ray based system that has an x-ray source to emit, for example, dual energy x-rays, a detector or an array of detectors that detect the emitted x-rays, and a conveyor system. The conveyor system has a conveyor belt that moves the article to be inspected through the emitted x-rays. The operator console includes a display device, an operator input device and a controller. The operator console is configured to provide information and control capabilities to an operator all within the same viewing field or arc. The operator console is configured to permit customization by individual operators and/or customization for a specific location where the inspection system is deployed (e.g., an airport or office building) without changing components. These features, as well as others, minimize operator fatigue, increase operator inspection speed and increase the efficiency of the inspection process. Further, this universal operator console configuration, enables the console to be interchangeable to various types of scanner systems produced by the assignee of the present invention as well as other manufacturers.

16 Claims, 8 Drawing Sheets

OPERATOR CONSOLE

OPERATOR CONSOLE FOR ARTICLE INSPECTION SYSTEMS

This is a continuation of application Ser. No. 08/647,043 filed May 08, 1996 now U.S. Pat. No. 5,699,400.

BACKGROUND OF THE INVENTION

1. Field of the Invention

The present invention relates to article inspection systems. More particularly, the present invention relates to article inspection systems having an operator console with improved operator interaction capabilities.

2. Description of the Related Art

Article inspection systems are used as security devices in airports, office buildings and the like to allow security personnel to inspect the contents of an article, e.g., baggage, for explosives, weapons or other contraband.

Early types of inspection systems were capable of detecting metal objects located in an article. More recently, automated x-ray based inspection systems have been developed that use single energy x-rays and dual energy x-rays to present an operator (e.g. security personnel) with an image of the objects within an article. Single energy x-rays typically present an image of the objects with shading representing varying degrees of mass density (i.e., opaqueness to x-rays). Dual energy x-rays, on the other hand, typically present an image with color proportional to the ratio of one energy band to the other on a pixel by pixel basis.

Such x-ray inspection systems incorporate a single or dual x-ray source, a scanning system, such as a conveyor, to move the article through an x-ray beam (e.g., a fan beam x-ray) to scan the article, a detector system that converts the x-ray flux which penetrates the article being inspected into pixels of values which represent the x-ray images(s) resulting from the scan, a processor, e.g., a computer or an array of processing elements used to control the operation of the x-ray source data and process the data, the scanning system and the detector system, and an operator interface (or operator console) that includes a display system that presents a black and white or color display of the resulting image of pixel values, and a operator input system that permits an operator to select various operational modes and to select various image enhancements of the inspection system.

An example of a currently used operator console has a display monitor that displays gray-scale images of the article, e.g., baggage, along with suspect area and target object overlays and other enhancements. The operator input system provides an operator with control over the display system using for example a zoom pad and touch pad icons.

However, in such operator consoles, both operator application data (e.g., the displayed image) and controls are not within the operator's same viewing field or arc, causing the operator to direct attention away from the display and toward the controls. This reduces the efficiency of the inspection process because of, for example, operator fatigue and/or time delays in completing the inspection process.

Another drawback of such operator consoles is that the touch pad icons are fixed and cannot be changed unless the pad itself is changed. As a result, various types of touch pads with different icons would have to be manufactured in order to provide different capabilities for the different environments where the inspection system may be used. In other words, current operator consoles cannot be operator and/or location customized without specific hardware changes. This also decreases the efficiency of the inspection process.

SUMMARY

The present invention provides an inspection system having a scanner system coupled to an operator console. The scanner system is preferably an x-ray based system that has an x-ray source to emit, for example, dual energy x-rays, a detector or an array of detectors that detect the emitted x-rays, and a conveyor system. The conveyor system has a conveyor belt that moves the article to be inspected through the emitted x-rays. The operator console includes a display device, an operator input device and a controller. The operator console is configured to provide information and control capabilities to an operator all within the same viewing field or arc. The operator console is configured to permit customization by individual operators and/or customization for a specific location where the inspection system is deployed (e.g., an airport of office building) without changing components. These features, as well as others, minimize operator fatigue, increase operator inspection speed and increase the efficiency of the inspection process. Further, this universal operator console configuration, enables the console to be interchangeable to various types of scanner systems produced by the assignee of the present invention as well as other manufacturers.

BRIEF DESCRIPTION OF THE DRAWINGS

Preferred embodiments of the invention are described hereinbelow with reference to the drawings wherein.

DETAILED DESCRIPTION

Generally, the present invention provides an article inspection system having a scanner system coupled to an operator console. The scanner system is preferably an x-ray ray based system that has an x-ray source to emit, for example, a fan-shaped beam or a movable pencil beam of single or dual energy x-rays through an article to be inspected, a radiation detector having a detector or an array of detectors that detect x-rays that penetrate the article, and a conveyor system that moves the article through the fan-shaped beam. The operator console includes a display device that displays the inspected article in various display modes (e.g., a normal display mode, a pseudo-color display mode, and a tri-material mode) and with various enhancements (e.g., 2× and 4× zoom, reverse video, edge enhancement, display contrast, etc.), a toolbar with various function icons, and an operator movable cursor. The operator console also includes an operator input device having control switches that, for example, control the operation of the conveyor system and a touch-sensitive pad (touchpad) that permits an operator to move the cursor with, for example a finger, to various icons provided on the toolbar and select a function associated with the icon by removing the finger from the touchpad. At least one controller is provided to control the operation of the scanner system and the operator console. The controller or controllers may be part of the scanner system or the operator console. Alternatively, the controller or controllers may be a separate unit, such as a personal computer or an array of processors, coupled to the scanner system and the operator console.

The operator console provides information and control capabilities to an operator all within the same viewing field or arc and is configured to permit customization by individual operators and/or customization for a specific location where the inspection system is deployed (e.g., an airport or office building) without changing components. These features, as well as others, minimize operator fatigue, increase operator inspection speed and increase the efficiency of the inspection process. Further, this universal operator console configuration is interchangeable with various types of scanner systems produced by the assignee of the present invention as well as other manufacturers.

Figure 1:
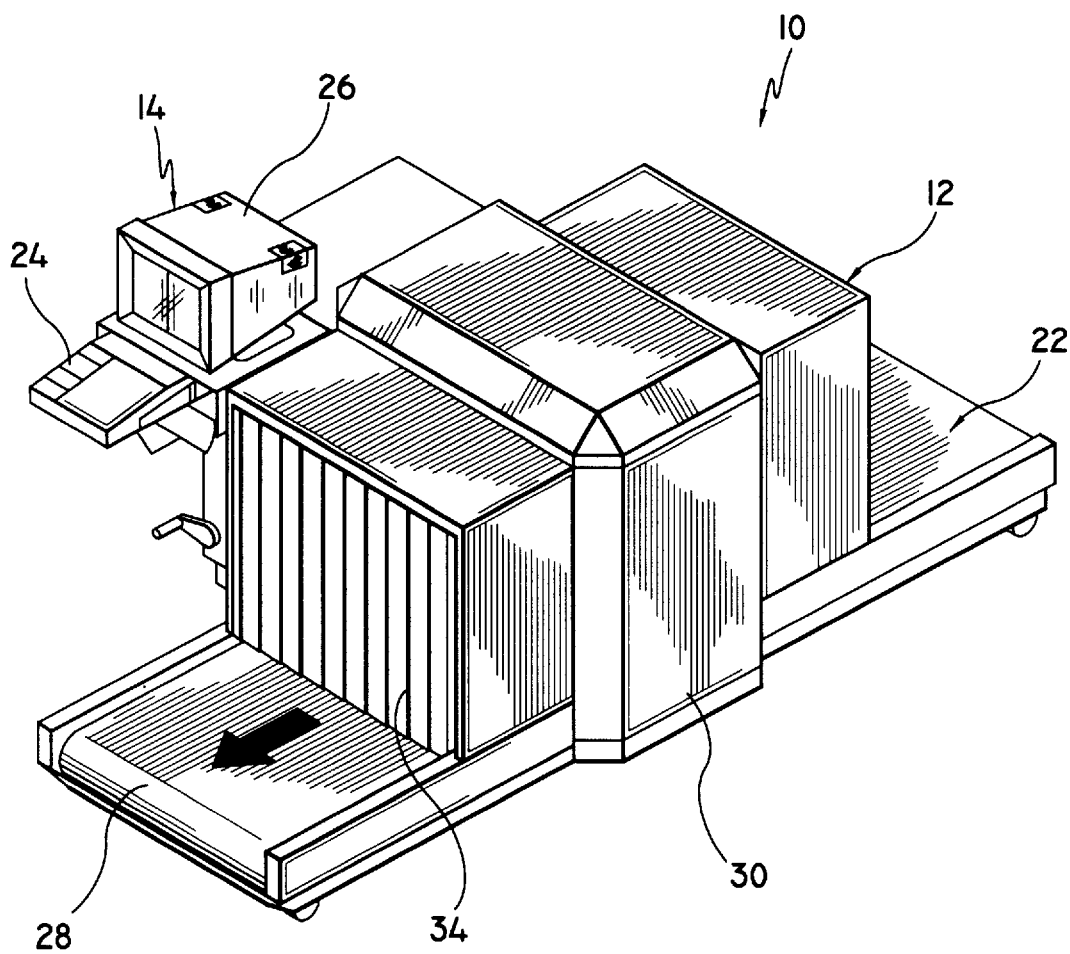
FIG. 1 is a perspective view of an exemplary embodiment of the article inspection system according to the present invention.
Figure 2:
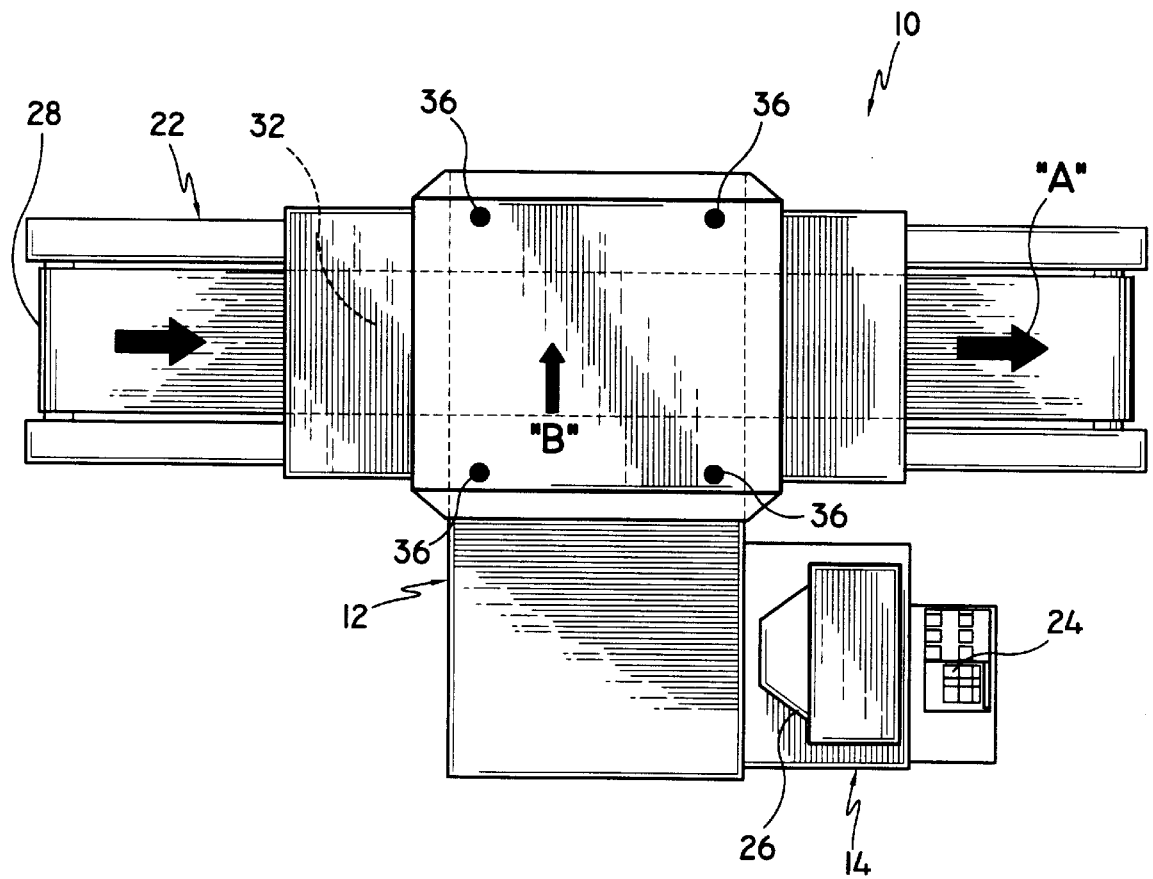
FIG. 2 is a top plan view of the article inspection system of FIG. 1.
Figure 3:
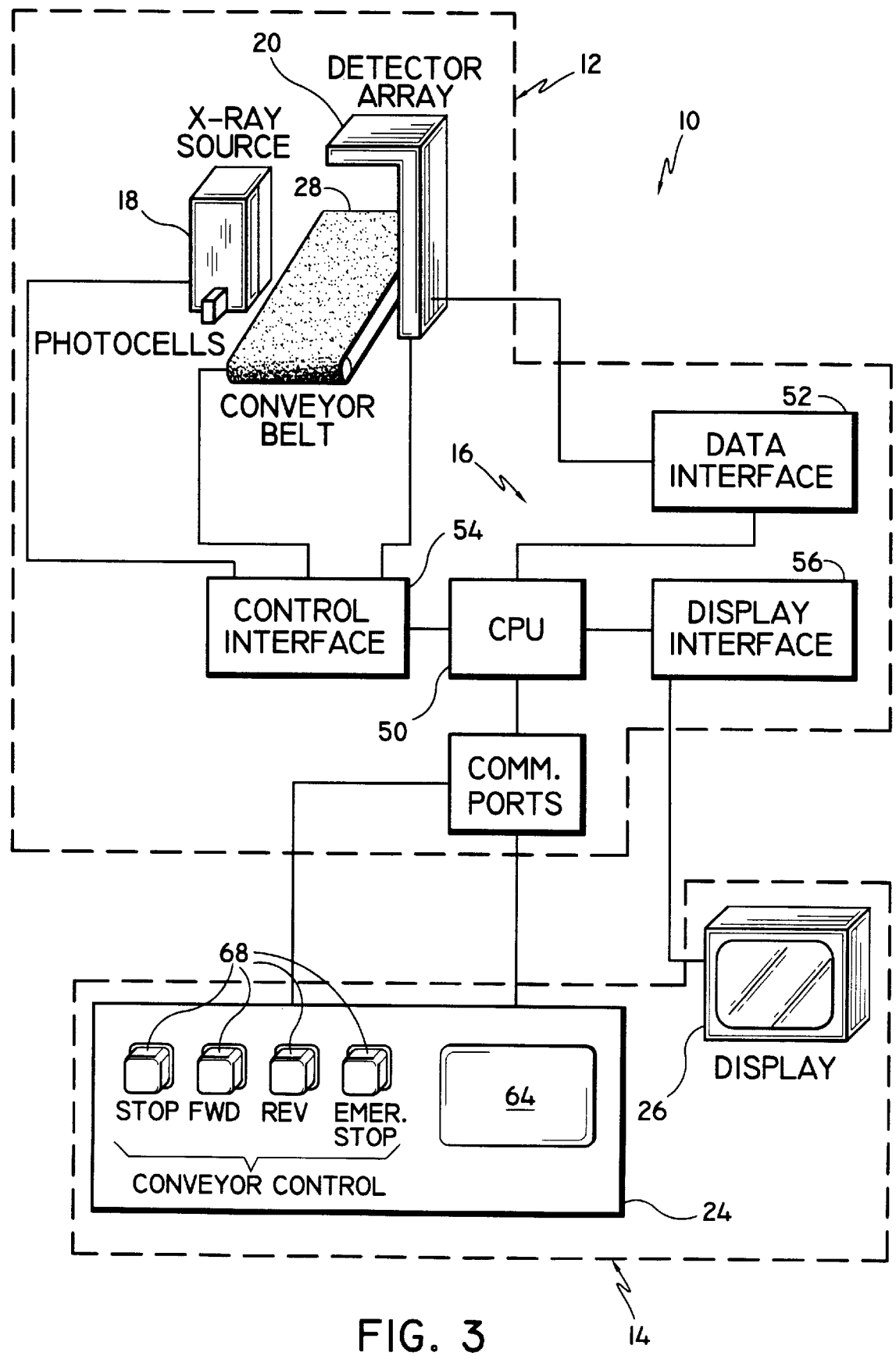
FIG. 3 is a block diagram of one configuration of the article inspection system according to the present invention.

Referring to FIGS. 1–3, the inspection system 10 of the present invention includes scanner system 12, an operator console 14 and a controller 16 which controls the operation of the scanner system and the operator console. The scanner system 12 utilizes an x-ray source 18, a radiation detector 20, and a conveyor system 22 to transport an article to a position between the x-ray source and radiation detector and scan the article. The operator console 14 includes an operator input device 24 and a display device 26. The conveyor system 22 has a conveyor belt 28 and associated belt drive mechanisms (e.g., a power roller not shown) that move the article through the x-ray beam.

Typically, the x-ray source 18 and the radiation detector 20 are enclosed in a common housing 30, seen in FIG. 1, and the conveyor belt 28 of the conveyor system 22 passes through a tunnel 32 in the housing 30 to move the article being inspected through a fan-shaped beam, or into position for scanning by a movable pencil shaped beam. Entrance and exit ends of the tunnel are blocked by lead curtains 34 to limit x-ray scatter. The tunnel 32 also includes a pair of article detector assemblies, e.g., photocells 36 which detect when an article enters the tunnel and when the article exits the tunnel. Indications from these article detector assemblies are transferred to the controller 16 and subsequently displayed on the display device 26 of the operator console so that the operator has an indication when the article enters and exits the tunnel. Thereafter, the operator can change the operation (or movement) of the conveyor belt 28 using control switches on the operator console.

In the embodiment of FIG. 3, the controller 16 is included in the scanner system 12, and the operator console 14 operates as a slave component to the scanner system. That is, the controller can be used to send image data associated with the article being inspected to the operator console, and to receive control information selected by an operator and control for example the conveyor system.

Figure 4:
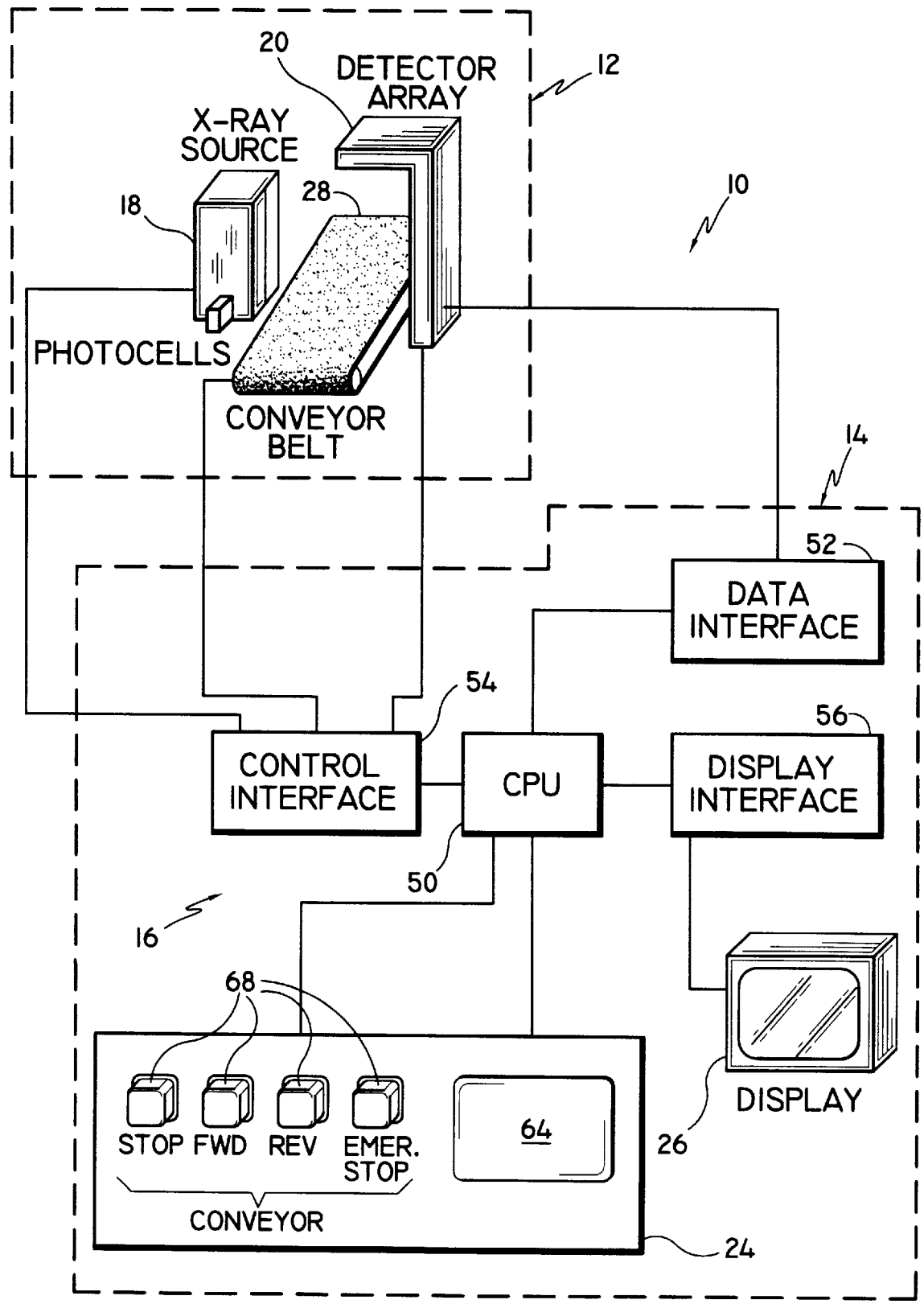
FIG. 4 is a block diagram of an alternative configuration of the of the article inspection system according to the present invention.

In an alternative embodiment shown in FIG. 4, the controller 16 is resident within the operator console 14, and the scanner system 12 operates as a slave component to the operator console. That is, the signals (scan data) generated by the radiation detector 20 are digitized and transferred using known data communication techniques to the operator console controller 16 which uses the image processor to processes the digitized signals into image data for display on the display device. As noted above, the controller may also be a separate unit that is coupled to both the scanner system and the operator console.

Figure 5:
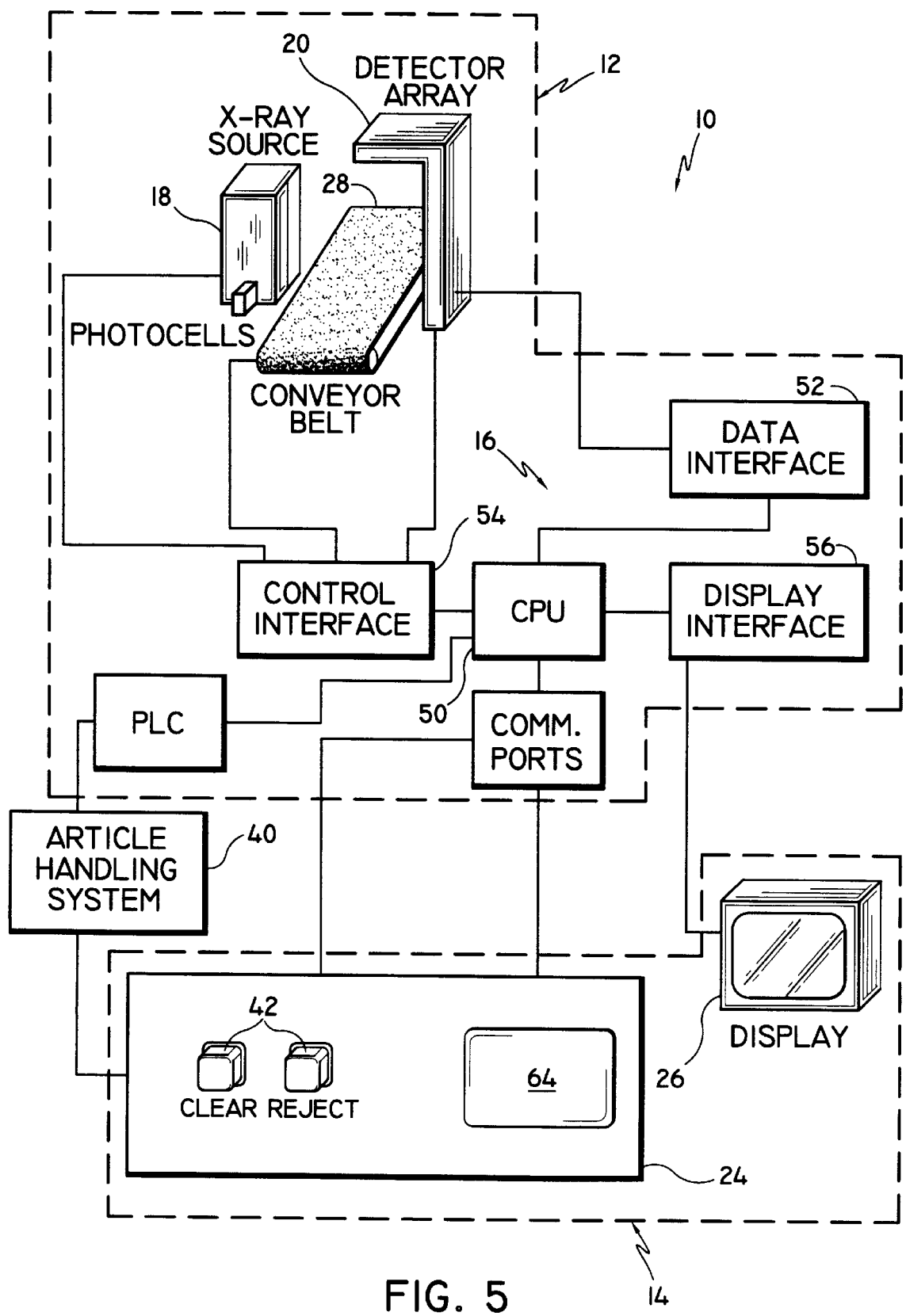
FIG. 5 is a block diagram of another alternative configuration of the article inspection system according to the present invention.

In another alternative embodiment shown in FIG. 5, the scanner system 12 and the operator console 14 are connected to an automatic article handling system 40 used to transfer inspected articles. For example, in automated airport baggage inspection systems passenger baggage is loaded onto the conveyor belt 28 of the conveyor system 22 for x-raying by the scanner system 12. After x-raying, the baggage is automatically transferred to the article handling system 40 and after an image of the contents of the baggage is displayed on a display screen of the display device 26, an operator makes a determination of whether the baggage clears inspection or is rejected by pressing one of the article handling system control switches 42. Activating one of the control switches will signal the baggage handling system to automatically transfer the baggage to either airplane cargo or to a baggage re-check area for further inspection, depending upon which switch is activated.

The controller 16 may be a single processor based unit or a unit having an array of processors. For the present discussion the term controller contemplates both configurations. As seen in the exemplary configuration in FIG. 3, the controller 16 includes a central processing unit (CPU) 50 having memory (e.g., RAM and ROM), stored programs (e.g., system and application programs), image processing circuitry to convert digitized radiation detector signals (scan data) into image data, and input/output circuitry to interface with other components of the article inspection system. The controller may be configured so that the CPU 50 is coupled to a data interface 52 connected to the radiation detector 20. The data interface 52 is a communication interface that formats digitized signals (scan data) from the radiation detector 20 for processing by the CPU 50. The data interface 52 provides the communication hardware to permit the controller 16 to interact with the various types of circuitry used in commercially available radiation detectors, such as the model VDS manufactured by Vivid Technologies, Inc. Thus, the controller 16 is independent of the various radiation detectors that can be used in the scanner system 12. A control interface 54 is coupled to the CPU 50 and is configured to send control signals to the scanner system conveyor and to receive, for example, system status signals from the various commercially available scanner systems components. A display interface 56 is coupled to the CPU 50 and is provided to format the image data processed by the CPU for display in various modes, and to provide general managing of the display device 26.

The controller may be an individual unit such as a personal computer having, for example, a Pentium® processor. Further, the processing system may include an array of high speed processors (e.g., a plurality of Pentium® based processors) which processes the digitized output signals from the radiation detector 20 and generates image data for displaying the article being inspected.

The x-ray source 18 generates and emits a fan-shaped beam or movable pencil beam of, for example, single energy or dual energy x-rays that penetrates articles being inspected. The article is x-rayed when moved through the beam by the conveyor system. Such x-ray sources are known and include an x-ray tube, associated high voltage power supply, and may include an internal sample reference system for verification. The x-ray source is controlled by the controller 16. In instances where the x-ray source emits a fan-shaped beam, the beam is preferably in a plane perpendicular to the direction of movement of the article passing through the beam. Thus, in the configuration of FIG. 2 the plane of the fan-shaped beam is perpendicular to the arrow "A" in the direction of arrow "B". However, the fan-shaped beam may be in a plane that is in other orientations relative to the direction of movement of the article being inspected. Examples of a dual energy x-ray inspection systems are described in U.S. Pat. Nos. 5,319,547 and 5,490,218 both of which are incorporated in their entirety herein by reference.

Radiation attenuated by the articles being inspected impinges the radiation detector 20 that may include a single detector or an array of detectors, which are preferably photodetectors. The output signals (scan data) from the radiation detector 20 may be analog signals that are subsequently digitized or they may be output by the radiation detector as digitized signals.

Figure 6:
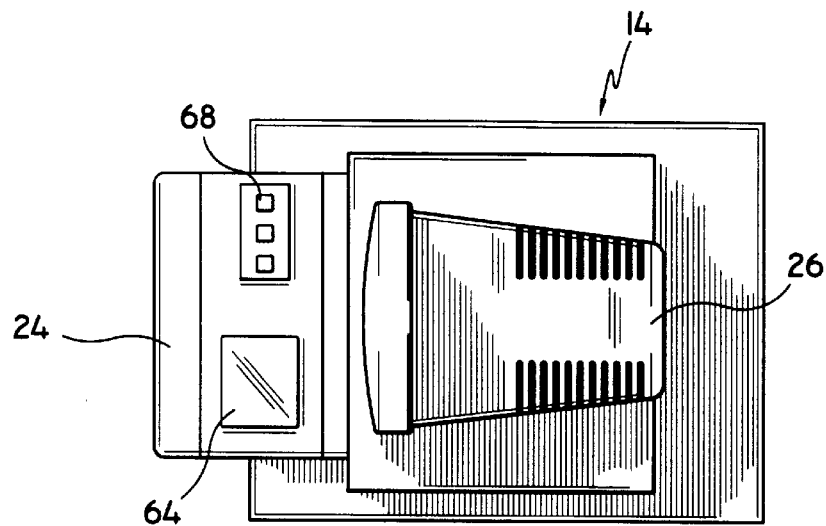
FIG. 6 is a top plan view of an operator console for the article inspection system according to the present invention.
Figure 7:
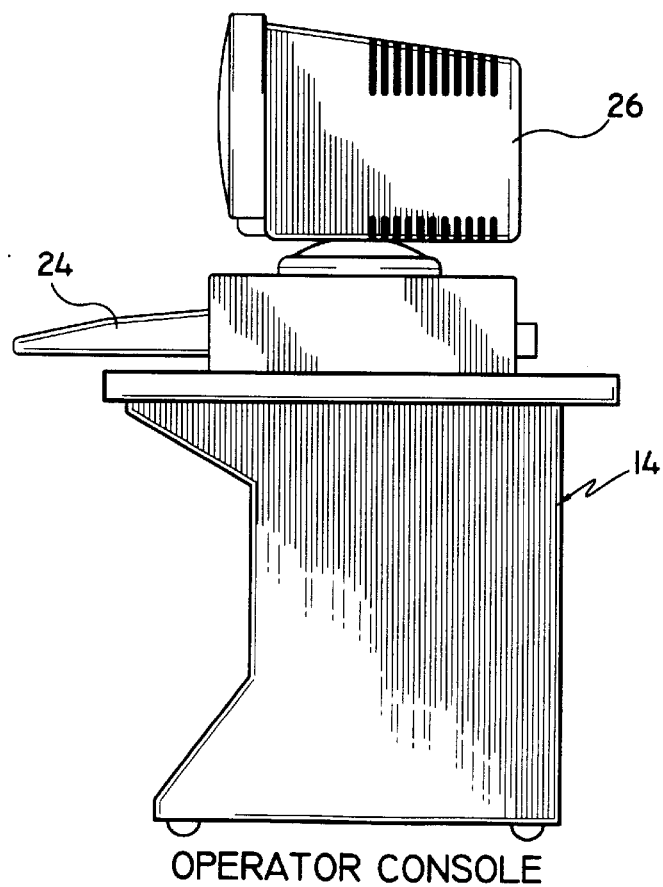
FIG. 7 is a side elevational view of the operator console depicted in FIG. 6.
Figure 8:
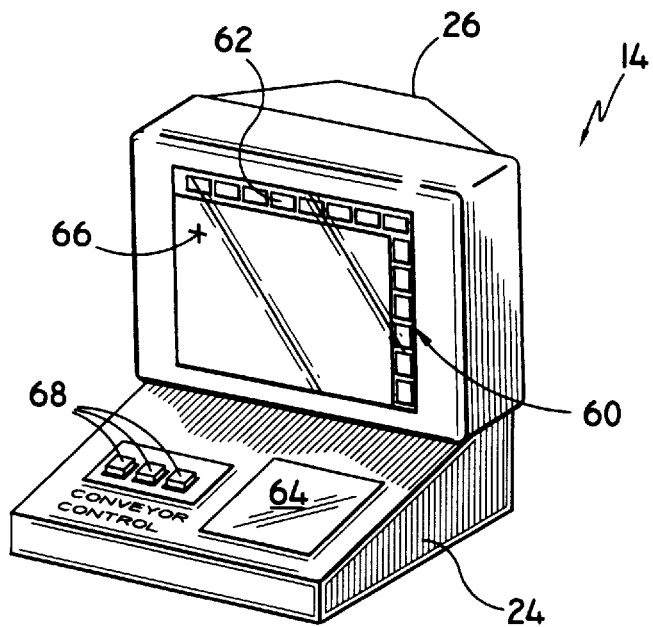
FIG. 8 is a perspective view of the operator console according to one embodiment of the present invention, illustrating conveyor control buttons on an operator input portion and a toolbar displayed on a display device.
Figure 9:
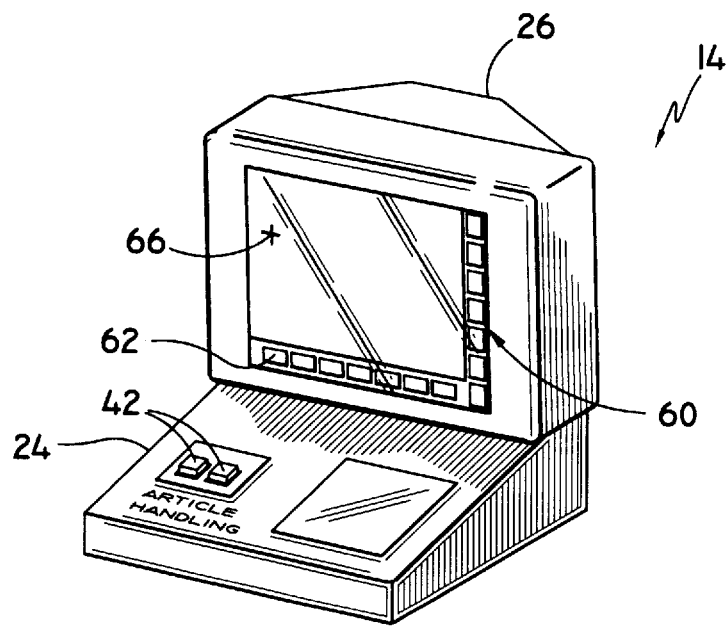
FIG. 9 is a perspective view of the operator console according to an alternative embodiment of the present application, illustrating article handling system control buttons on the operator input portion.
Figure 10:
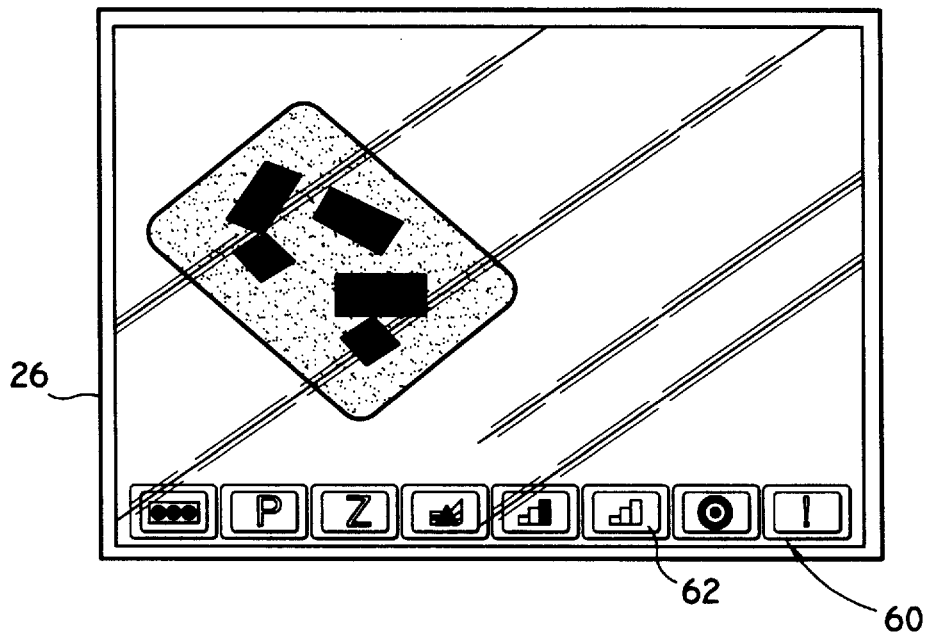
FIG. 10 is an exemplary diagram for a display of an article being inspected and a toolbar.
Figure 11:
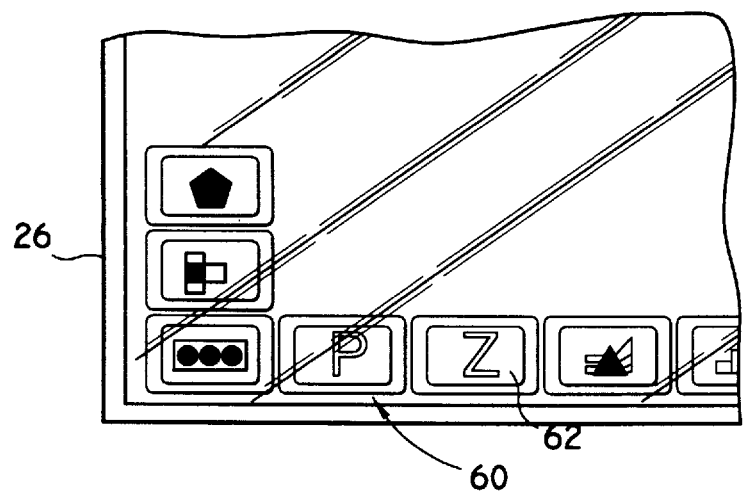
FIG. 11 is an enlarged view of a portion of the display of FIG. 7, illustrating icons in the toolbar.

Referring to FIGS. 3, 6 and 7, the operator console 14 includes a display device 26 and an operator input device 24. The display device is preferably a high-resolution video monitor having a resolution of, for example 1280 pixels× 1024 pixels, or 1024 pixels×768 pixels. The display device can be configured to display a toolbar 60, seen in FIGS. 8 and 9, which includes a plurality of icons 62 that may be displayed all the time or that may be selectively displayed when, for example, the operator touches touchpad 64. Selection of a function associated with the icons is made using a virtual cursor 66 and the touchpad 64 associated with the operator input device 24, as will be discussed below.

In the embodiment of FIGS. 3 and 4, the operator input device 24 includes a plurality of conveyor control switches 68 which permit an operator to control movement of the conveyor belt 28. For example, the conveyor control switches may be used for conveyor forward, conveyor reverse, conveyor stop, and emergency stop functions. In the embodiment of FIG. 5, the operator input device includes a plurality of article handling control switches 42 which when activated sends signals to clear or reject the article in the article handling system 40 depending upon which switch is activated.

As noted, the operator input device 24 also includes the touchpad 64 that is provided to permit an operator to select icon functions displayed in the toolbar without changing the operator's field of view. The touchpad 64 is a touch-sensitive glass or plastic panel coupled to the controller 16. The controller converts the location of, for example, an operator's finger on the panel into X-Y coordinates and translates the coordinates into pixel locations on the display device screen. A cursor 66, seen in FIG. 6, is displayed at the pixel locations on the display device 32. By processing the change in the X-Y coordinates which occurs with movement of the operator's finger, the cursor 66 moves on the display device. If the cursor 66 is positioned on an icon 62, withdrawal of the finger from the touchpad selects the function associated with the icon. Alternatively, the operator could select the function by depressing the icon or double-clicking the icon or the like. An example of a suitable touchpad is the model 13-4051 flat sensor manufactured by MicroTouch Systems, Inc.

Various types of icons may be used in the system of the present invention and arranged in a customized order on the display device 26 by each operator. Examples of commonly used icons and their function include display mode icons, threat detection icons, image enhancement icons, and object analysis icons. Common display mode icons permit the operator to select between, for example, normal, pseudo-color and tri-material display modes which provide predefined color shading or color scaling to the image displayed. Common threat detection icons include for example a blasting cap icon, a threat icon and a density alert icon. If an operator views a suspicious item on the display device, selection of one of the threat icons enhances the displayed image to show by, for example, color scaling or crosshair that the suspected item has the characteristics of a functional bomb, that the item is a suspect item or an alarm item, or that the density of the suspect item is too dense to penetrate sufficiently for an accurate analysis. Common image enhancement icons permit the operator to select between various image enhancement functions, such as an edge enhancement function which when activated accentuates the edges between objects in the article being inspected, a reverse video function which inverts a gray-scale image, and a display contrast function that displays the image of the article at either a high, medium or low contrast setting. Common analysis icons include "P" and "Z" analysis functions. The "P" analysis function permits an operator to see, for example, explosive components that may be hidden within a target material by suppressing the image of the target material and highlighting the explosive components. The "Z" analysis function permits an operator to separate an image of the article into objects having low atomic numbers and objects having high atomic numbers, where the objects having the high atomic numbers are suppressed so that the objects with low atomic numbers can be seen.

As noted above, the article inspection system of the present invention can be configured to allow different operators to customize the icon arrangement in the toolbar and the location of the toolbar on the display screen for their particular preferences. Each customized toolbar is then stored in memory and an operator can recall their toolbar at, for example, the beginning of their work shift. In addition, the toolbar can also be customized for a particular operational environment (e.g., an airport or office). This location customized toolbar can be stored in memory and retrieved by an operator for subsequent use.

An example of the inspection process for the article inspection system of the present invention will now be discussed. After system power-up and initialization, the controller enters an operation mode where the display device 26 shows a blank screen, except for the toolbar, and the controller periodically polls the components of the scanner system 12 and the operator console 14 for interrupts. That is, controller periodically polls each component to determine if action is required. For example, the controller periodically polls the touchpad 64 to determine if the operator has placed a finger on the plate. As another example, the controller periodically polls the article detector assemblies 36 to determine if an article is entering or exiting the housing tunnel 32.

If an article is placed on the conveyor belt 28 the operator then starts the belt using the conveyor control switches 68 on the operator input device 24. When the article passes the article detector assembly 36 at the entrance of the tunnel 32, the x-ray source and radiation detector are activated. Radiation (scan) data is collected at a rate of, for example, four (4) lines every 16.666 ms. The controller periodically polls the data interface unit for the presence of new inspection data and categorizes the new data as an air or item line. Air lines are detected lines of x-rays without x-rays penetrating the article. Air lines just prior to the article passing through the x-ray beam and/or lines of x-rays just after the article has passed through the beam are of particular interest. For example, air lines just prior to the x-rays passing through the article provide a noise floor for each article inspected. As the article begins to pass through the x-ray beam the first item line is marked as a begin item line and the air sample preceding the begin line is averaged and subtracted from each item line for the article being inspected. Every item line is then stored as scan data and transferred to the image processor in the controller and converted into image data for subsequent display on the display device. The operator views the image displayed on the display device to determine if any of the objects in the article are suspect items or target objects necessitating further inspection. Target objects typically include explosives, weapons and the like.

If during any point in the inspection process the operator touches the touchpad to, for example, change the display mode, the touchpad will generate an interrupt which is detected by the controller when polled. A predetermined number of bytes of coordinate data is stored in an operator input device buffer and the cursor 66 is then displayed. Movement of the cursor is also drawn on the display device and when the operator withdraws the finger from the touchpad, the function associated with the icon where the cursor was last positioned is performed. The display device then begins displaying the image data in the new display mode.

When the last line of the article passes through the x-ray beam, the controller marks the item line as an end item line and polls the article detector assembly 30 at the exit end of the tunnel to determine if it is activated. If the detector assembly is activated the controller instructs the interface unit to deactivate the x-ray source and the radiation detector.

It will be understood that various modifications can be made to the embodiments of the present invention herein without departing from the spirit and scope thereof. For example, various types of scanner systems and conveyor systems from various manufacturers may be used and various configurations for the components of the system may be implemented. Therefore, the above description should not be construed as limiting the invention, but merely as preferred embodiments thereof. Those skilled in the art will envision other modifications within the scope and spirit of the invention as defined by the claims appended hereto.

What is claimed is:

1. An article inspection system comprising:
    a scanner system scanning an article with penetrating radiation that penetrates the article to detect characteristics of an interior volume of the article;
    an operator console coupled to said scanner system, said operator console including a display device configured to display an image of said interior volume of the article scanned by said scanner system, a toolbar and a cursor; and
    an operator input device having at least one control switch and a touchpad responsive to touch of an operator's body part,
    wherein said scanner system in combination with said operator console scans the article with said penetrating radiation and displays an image of objects in said interior volume of the article, and said toolbar has function icons which when selected perform a predefined function, and said cursor is responsive to movement of the operator's body part on said touchpad to permit the operator to select a function associated with said icons while maintaining visual contact with the images of said interior volume of the article being scanned on said display device.

2. The article inspection system according to claim 1, wherein said toolbar is configurable by individual operators to display selected function icons in a selected order.

3. The article inspection system according to claim 1, wherein said at least one control switch comprises conveyor control switches.

4. The article inspection system according to claim 1, further comprising an article handling system that transports inspected articles to operator designated locations.

5. The article inspection system according to claim 4, wherein said at least one control switch comprises article handling control switches that designate the location an inspected article is transported to by said article handling system.

6. The article inspection system according to claim 1, wherein said scanner system includes a controller coupled to said operator console and provided to control the operation of said scanner system to scan the article with said penetrating radiation, to receive scan data of the article from said scanner system, to process said scan data for display, and to transfer said processed scan data to said operator console for display.

7. The article inspection system according to claim 1, wherein said penetrating radiation comprises x-rays and said scanner system comprises a dual energy x-ray scanner scanning the article with x-rays and a detector system receiving x-rays which have interacted with the article.

8. The article inspection system according to claim 1, wherein said article inspection system includes a separate controller coupled to said scanner system and said operator console and provided control the operation of said scanner system to scan the article with said penetrating radiation, to receive scan data from said scanner system, to process said scan data for display, and to transfer said processed scan data to said operator console for display.

9. An article inspection system comprising:
    a scanner system scanning an article with penetrating radiation that penetrates the article to detect characteristics of an interior volume of the article;
    an operator console coupled to said scanner system, said operator console including a display device configured to display indicia of said characteristics of said interior volume of the article scanned by said scanner system, a toolbar and a cursor; and
    an operator input device having at least one control switch and a touchpad responsive to touch of an operator's body part,
    wherein said scanner system in combination with said operator console scans the article with said penetrating radiation and displays said indicia, and said toolbar has function icons which when selected perform a predefined function, and said cursor is responsive to movement of the operator's body part on said touchpad to permit operator selection of a function associated with said icons while maintaining visual contact with said indicia of said interior volume of the article being scanned on said display device.

10. The article inspection system according to claim 9, wherein said toolbar is configurable by individual operators to display selected function icons in a selected order.

11. The article inspection system according to claim 9, wherein said at least one control switch comprises conveyor control switches.

12. The article inspection system according to claim 9, further comprising an article handling system that transports inspected articles to operator designated locations.

13. The article inspection system according to claim 12, wherein said at least one control switch comprises article handling control switches that designate the location an inspected article is transported to by said article handling system.

14. The article inspection system according to claim 9, wherein said scanner system includes a controller coupled to said operator console and provided to control the operation of said scanner system to scan the article with said penetrating radiation, to receive scan data of the article from said scanner system, to process said scan data for display, and to transfer said processed scan data to said operator console for display.

15. The article inspection system according to claim 9, wherein said penetrating radiation comprises x-rays and said scanner system comprises a dual energy x-ray scanner scanning the article with x-rays and a detector system receiving x-rays which have interacted with the article.

16. The article inspection system according to claim 9, wherein said article inspection system includes a separate controller coupled to said scanner system and said operator console and provided to control the operation of said scanner system to scan the article with said penetrating radiation, to receive scan data from said scanner system, to process said scan data for display, and to transfer said processed scan data to said operator console for display.

* * * * *